United States Patent [19]

Barnhurst et al.

[11] 4,110,426

[45] Aug. 29, 1978

[54] METHOD OF TREATING SKIN AND HAIR WITH A SELF-HEATED COSMETIC

[75] Inventors: James Douglas Barnhurst, Millington; Durland Karl Shumway, Piscataway, both of N.J.

[73] Assignee: Colgate-Palmolive Company, New York, N.Y.

[21] Appl. No.: 663,941

[22] Filed: Mar. 4, 1976

Related U.S. Application Data

[63] Continuation-in-part of Ser. No. 382,066, Jul. 24, 1973, abandoned, which is a continuation of Ser. No. 56,244, Jul. 17, 1970, abandoned, which is a continuation of Ser. No. 560,055, Jun. 24, 1966, abandoned.

[51] Int. Cl.$^2$ .................. A61K 9/14; A61K 7/15; A61K 7/48
[52] U.S. Cl. ........................................... 424/46; 424/47; 424/70; 424/73; 424/185; 424/69
[58] Field of Search .................. 424/46, 47, 70, 73, 424/185

[56] References Cited

U.S. PATENT DOCUMENTS

| | | | |
|---|---|---|---|
| 3,014,061 | 12/1961 | Irish et al. | 260/462 R |
| 3,030,196 | 4/1962 | Dykstra | 260/462 R |
| 3,103,532 | 9/1963 | Dykstra | 260/462 |
| 3,341,418 | 9/1967 | Moses | 424/73 X |
| 3,378,504 | 4/1968 | Lee | 260/2 |

FOREIGN PATENT DOCUMENTS 818,925 8/1959 United Kingdom .................. 424/185

OTHER PUBLICATIONS

Hawthorne, Chem. Abs., 1958, vol. 52, p. 7190.
Tikhmener, Chem. Abs., 1957, vol. 51, pp. 7827–7828.
Meschi et al., Chem. Abs., 1961, vol. 55, pp. 4123, 4124.

*Primary Examiner*—Dale R. Ore
*Attorney, Agent, or Firm*—Herbert S. Sylvester; Murray M. Grill; Norman Blumenkopf

[57] ABSTRACT

Nonaqueous compositions, especially cosmetic preparations such as shaving creams, are rendered self-heating by including therein a compound containing at least one boron-oxygen-boron linkage, such as triethoxyboroxine, which reacts exothermically with water or other protic material.

8 Claims, No Drawings

METHOD OF TREATING SKIN AND HAIR WITH A SELF-HEATED COSMETIC

This application is a continuation-in-part of our application Ser. No. 382,066 filed July 24, 1973, which was a continuation of our application Ser. No. 56,244 filed July 17, 1970, and both are now abandoned, which was in turn a continuation of our application Ser. No. 560,055 filed June 24, 1966, and now abandoned.

This invention relates to a novel method of chemically heating substrates by applying thereto a novel self-heating composition containing as the essential ingredient a compound containing at least one boron-oxygen-boron chemical bond. These compositions include facial cleaners, skin creams, lotions, soaps, detergents, shampoos, topical pharmaceuticals, shaving and after-shave preparations, and aerosol shave cream formulations, all of which produce heat by chemical action with water or other protic solvent to provide a hot cosmetic composition.

In the use of many cosmetic preparations it is desirable to apply a hot or warm composition. In some cases, where warmth has a soothing effect, it is more pleasant to apply a warm composition to the skin than a cold one. For example, application of a lotion to the dorsal area prior to beginning a back-rub is generally unpleasant because of the low temperature of the lotion. On the other hand, if a warm lotion were applied, the back muscles would immediately relax and the recipient would be comfortable.

It is well known that a better and more comfortable shave can be obtained when the skin in the area to be shaved has been heated. By heating the skin, the hair is softened allowing smoother passage of the razor blade therethrough. For many years barbers have applied a hot towel prior to applying shaving cream. Barber shops have been provided with apparatus for dispensing heated shaving cream, but these units have been uneconomical for use by the average person who shaves at home.

A large majority of men have adopted the use of aerosol shave bombs as a source of shaving cream for home utilization. These cans are pressurized to provide a means for dispensing the shaving cream and for forming a foam product. Shaving creams dispensed from aerosol bombs have heretofore been at room temperature, or below because of the vaporization of the propellant, and the aerosol container could not be heated to provide warm lather because of the explosive hazards due to the presence of pressurized gases.

The desirability of hot shave preparations has been recognized in the art. Accordingly, a recent development in this field utilizes a heat exchange unit built into the cap of an aerosol dispenser which is activated by hot tap water contacting the outside of said cap. The shaving cream released from the aerosol dispenser travels through, and is heated by, the heat exchange unit prior to its application to the skin. This is a mechanical means of heating and dispensing hot shave preparations.

It has now been discovered that a self heating cosmetic preparation can be produced by including in the preparation a compound which reacts exothermically upon contact with water. Accordingly, the user of the preparation need only moisten his skin in the area to be treated, and then apply the preparation at room temperature whereupon the chemical reaction between the water and the novel composition of this invention produces a predetermined desired amount of heat to thereby provide a pleasant warming sensation, and in the case of a shaving preparation, to provide the concomitant softening of the beard.

These self heating compositions must meet certain standards in order to be usable as a cosmetic preparation. The most important requirements are that said composition be non-toxic and non-irritating to the skin since it is applied directly thereto. Another essential requirement is that during the evolution of heat, no noxious or malodorous fumes are released. Still another necessary feature of these formulations is the ability to easily and readily wash the skin free therefrom.

Accordingly, a primary object of the present invention is to provide a self heating cosmetic composition.

Another object of the instant invention is to provide a non-toxic, non-irritating self-heating cosmetic preparation.

Still another object of the instant invention is to provide a cosmetic composition containing a compound which reacts exothermically with water or other protic material without releasing noxious or malodorous fumes during said evolution of heat.

A further object of the instant invention is to provide a self-heating cosmetic composition capable of being readily washed off from the skin.

Another object of this invention is to provide a method of chemically producing heat.

More specifically the present invention relates to a self-heating composition and a method of chemically producing heat by contacting said composition containing a boron compound having at least one boron-oxygen-boron bond with a protic material, whereby an exothermic reaction occurs between the boron compound and the protic material.

The term protic material includes any substance having a proton for reaction with the boron compound. Included in this group is water; lower aliphatic alcohols such as methanol, ethanol, propanol, isopropanol, butanol, octanol, lower amines, except tertiary amines such as n-butyl amine; lower alkanol amines such as triethanol amine; aliphatic acids such as acetic acid, propionic acid; polyols such as glycerine, propylene glycol, diethylene glycol, triethylene glycol, etc. and derivatives thereof having a reactive proton such as ethylene glycol monoethyl ether.

The boron containing compound which reacts with the protic material is an exothemic reaction is selected from the class consisting of boric oxide and compounds defined by the formula:

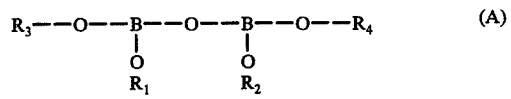

wherein $R_1$, $R_2$, $R_3$ and $R_4$ each is selected from the group consisting of an alkyl, aryl, aroyl, cycloalkyl, acetyl, aralkyl, and ethoxylated alkyl, aryl, acetyl, aralkyl, aroyl, and cycloalkyl group, and $R_1$ and $R_3$ taken collectively and $R_2$ and $R_4$ taken collectively is selected from the group consisting of

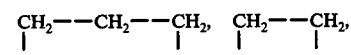

-continued

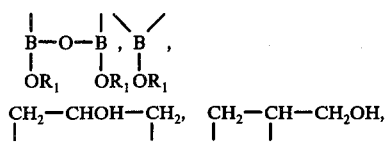

whereby cyclic compounds may be formed.

Boric oxide can be also defined by the above formula, wherein $OR_1$ and $OR_3$ collectively and $OR_2$ and $OR_4$ collectively is = O.

Compounds having B—C and B—H bonds should be excluded because they may oxidize with explosive force. In addition, such compounds are toxic.

Configurations of the boron-oxygen portion of the materials utilizable herein include:

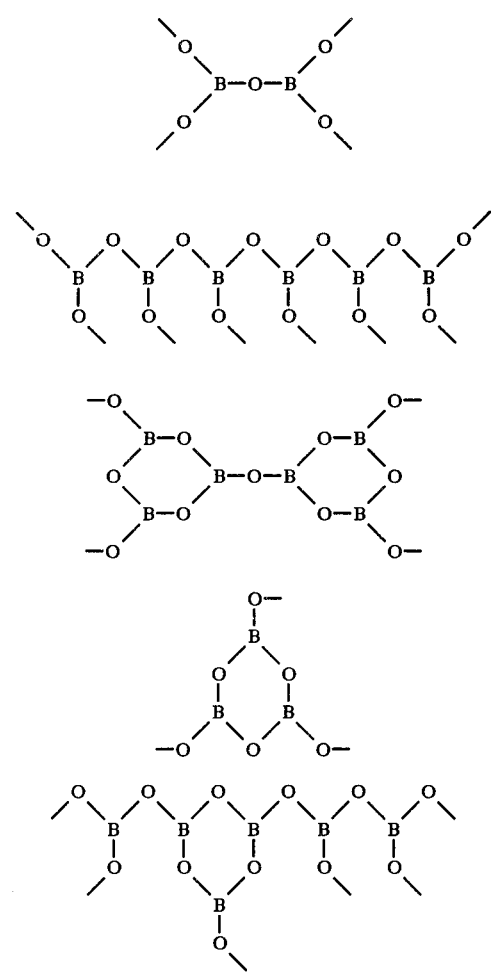

(I) Configurations wherein the R group is an alkyl radical:

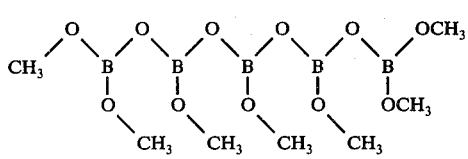

(a)

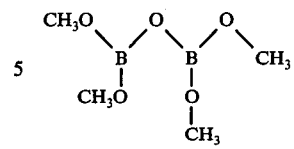

(b)

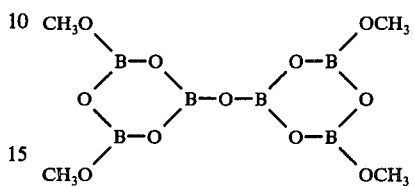

(c)

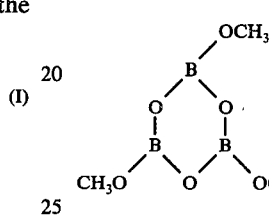

(d)

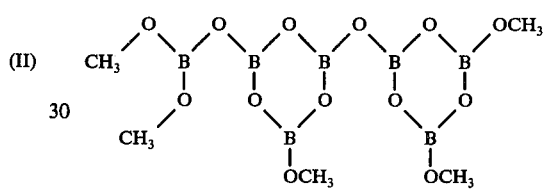

(e)

(2) R is an aryl group:

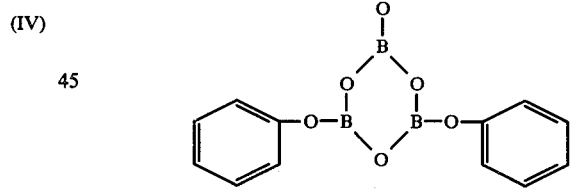

(3) R is an aroyl group:

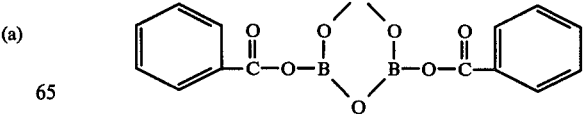

(4) R is an Aralkyl radical:

(5) R is a cycloalkyl radical:

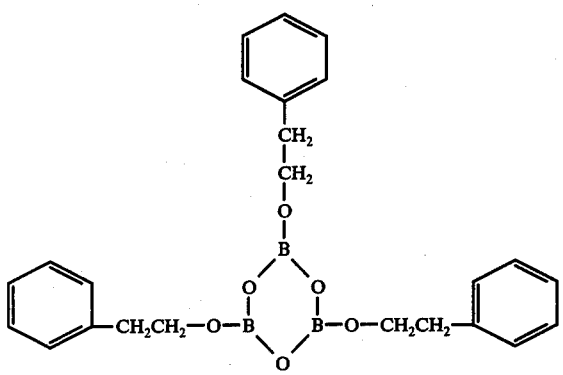

(6) R is an acetyl group:

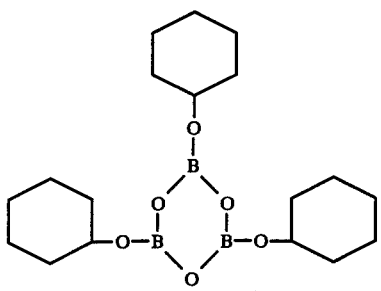

(7) R is an ethoxylated alkyl group:

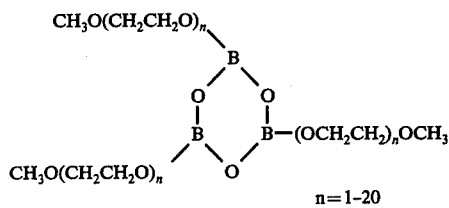

(8) R is an ethoxylated aralkyl group:

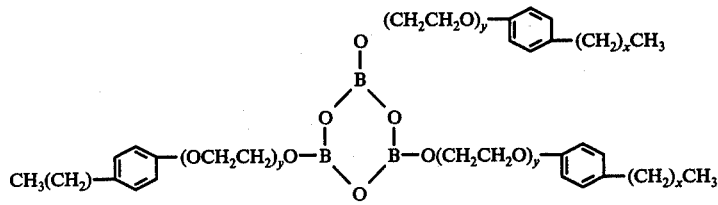

y=1-20

Many more structural configurations, not listed herein, are also contemplated by this invention.

Specific compounds included in the instant invention are:

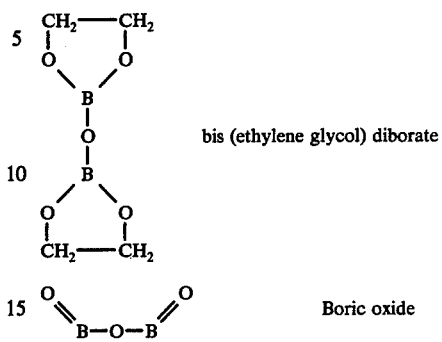

bis (ethylene glycol) diborate

Boric oxide tetraacetyl diborate,

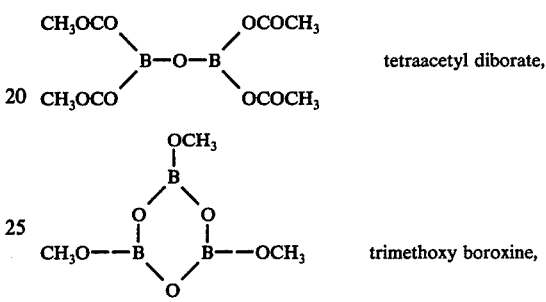

trimethoxy boroxine, dimers, trimers and polymers thereof. When trimethoxyboroxine is warmed in vacuo, trimethyl borate is liberated as the boroxine is polymerized, yielding a viscous mass which is also capable of releasing heat in the presence of a protic material.

The splitting of the boron-oxygen bond releases heat with the formation of boric acid and an alcohol in accordance with following when using trimethoxyboroxine.

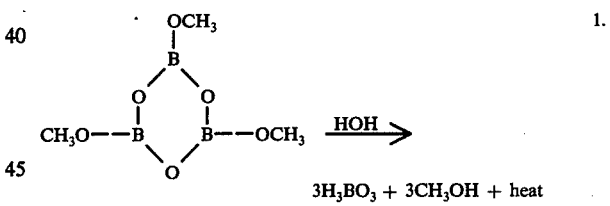

1.

$3H_3BO_3 + 3CH_3OH +$ heat

Other alcohols are formed when substituting ethyl, propyl or other groups for the methyl group. In addition acetic acid, phenol, etc. is formed in lieu of the alcohols by substituting other organic radicals for the $CH_3$ group.

Similarly, tetracetyl diborate reacts with water to release heat in accordance with the following equation:

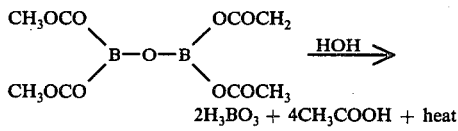
$$2H_3BO_3 + 4CH_3COOH + \text{heat}$$

In the above reaction boric acid and acetic acid are formed. The substitution of other organic radicals for the acetyl radical would result in the formation of other acids, alcohols, or the like, the only limitation being that the reaction products are not toxic. As the weight of the radicals attached to the B—O—B nucleus increases, its reactivity with a protic material to release heat decreases, and the heat released per unit weight of boroxine decreases, i.e. the methyl radical is more reactive and yields more heat than the ethyl radical; the ethyl radical is more reactive and yields a greater amount of heat than the octyl radical; and so forth.

The rate and degree of heat liberated is dependant on the specific protic material, the particular boron compound and the inert extending medium utilized. For example trimethoxy-boroxine, which is a liquid, liberates heat quickly when diluted with water. Solid boron compounds containing at least one B—O—B bond release heat at different rates depending on the particle size, i.e. gross particles liberate heat slowly whereas finely divided particles result in a more rapid release of heat (i.e. 5 gms. of boric oxide wafers caused a temperature increase of 26° whereas 5 gms. of crushed wafers caused a temperature increase of 31°, each in contact with 5 gms. of water for 5 minutes). It has also been found that the rate and degree of heat released varies for each type of protic material as well as for members of a homologous series of a protic solvent. For example, in the fatty alcohol series, the rapidity of heat release is inversely proportional to the chain length of the alcohol. The variations in the degree of heat liberation when using various protic solvents with trimethoxyboroxine is shown in Table I, wherein 5 ml. of a protic solvent was added to 5 ml. trimethoxyboroxine in a series of test tubes. Each mixture was stirred and the temperature change measured with a thermocouple until the maximum temperature was reached. The following results were obtained:

Table I

| Solvent | Starting Temp., C° | Max. Temp., C° | ΔT, °C |
|---|---|---|---|
| Water | 20.5 | 70.5 | 50 |
| Methanol | 20.5 | 42 | 21.5 |
| n-Butyl amine | 23.0 | 83 | 60 |
| n-Butanol | 21.0 | 36 | 15 |
| 1-dodecanol | 20.0 | 28 | 8 |

This data shows that water and n-butyl amine release the greatest amount of heat, rendering said combination with TMB particularly useful where hot applications are desired. If only warmth is desired rather than substantial heat, TMB may be mixed with n-butanol, methanol or 1-dodecanol. Thus, it is apparent that the degree of heat liberated and the rate of heat released would dictate the particular combination of boron compound and protic material. In addition, the presence of the extending medium can either hinder or accelerate the liberation of heat. Thus, it is apparent that multiple factors influence the amount and rapidity of heat released with the compositions of this invention. However, in many situations, there is a need for a composition capable of releasing heat, the amount thereof being inconsequential.

The boroxines are excellent heat generating materials and may be prepared by reacting boric oxide with an organic alcohol such as a lower aliphatic alcohol in accordance with the following equations:

propyl or isopropyl alcohol + boric oxide ——> tripropoxy-
boroxine or triisopropoxyboroxine

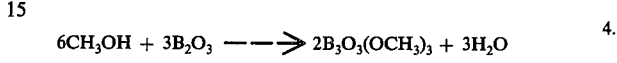
methanol + boric oxide ———> trimethoxyboroxine

The trimethoxyboroxine is a liquid at room temperature, whereas the tri-isopropoxyboroxine is a solid at room temperature. The higher aliphatic alcohols also react with boric oxide to yield a boroxine in accordance with the following equation:

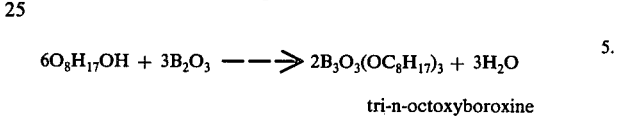
tri-n-octoxyboroxine

The tri-n-octoxyboroxine is a viscous liquid at room temperature.

The aforesaid boron compounds are incorporated into a cosmetic composition so that upon application thereof to the skin in the presence of even a small amount of water, the area becomes warm and beneficial effects are obtained. The application of self heating facial cleaners, skin creams and lotions is obviously beneficial since the warmth affords superior cleansing and conditioning action and generally tônes up the skin. An important advantage of the use of self-heating soap and detergent compositions resides in the fact that there is no need for warm or hot water when washing either one's self or fabrics or the like because of local generations of heat at the site of application. This is especially useful in areas where warm water is unavailable such as when our armed forces are in the field or campers and hunters are in the woods.

These boron-containing compositions can also be used as cleansing formulations for body cavities such as teeth, mouth, eyes, rectal and vaginal cavities, said compositions becoming warm during usage. Similarly, a shampoo would generate its own heat upon contact with damp hair.

Therapeutic effects can also be obtained by topical or internal application of these formulations. Examples of therapeutic applications include the alleviation of sore muscles, aching joints, tired eyes, fungal and bacterial infections, rashes, bruises, wounds, sore throats, etc..

Other uses for the boron-containing compositions include the warming of certain protic solvents being used or to be used as a heating bath for various animate and inanimate objects floating, suspended or immersed in the solvent. Continued heat could be released for these purposes by delivering the heat generating material to the bath over a prolonged period of time. Another use would be as a desiccant for liquids, solids and gases. Safety devices designed to signal danger or trip emergency equipment switches may utilize the heat generating formulation and method of the instant invention.

In frigid climates, or where warm water is unavailable, the instant heat generating method and compositions would be useful in melting ice, in providing instant warmth for personnel, animals and equipment, in warming moving and stationary parts of machinery, in warming lubricants.

Textiles, paper, plastics and films of all kinds can be coated or impregnated with compositions containing the boron compound of this invention.

The self-heating cosmetic compositions of the present invention may be prepared in a variety of physical forms. They may be liquids, pastes, solids, and powders. They may constitute a single oleaginous phase or may comprise an emulsion of two non-aqueous phases made miscible by agitation (i.e. mineral oil and trimethoxyboroxine), or a dispersion of a solid in a non-aqueous liquid phase. The composition may exit in the form of a dual phase (aqueous and oleagenous) if each phase is contained separately and is admixed only at the site of application.

Accordingly, the heat-generating boron compound may be incorporated into any non-aqueous inert carrier or extending medium which is non-reactive with the boron-oxygen-boron containing compound. Suitable inert carriers or extending media include particulate solids such as polyethylene and other inert organic polymers and aluminum oxide and other inert inorganic materials, inert solvents such as straight chain, branched, cyclic saturated and unsaturated hydrocarbons such as benzene, toluene, mineral oil, etc., glycol ethers such as diethylene glycol dimethyl ether; ethers such as diethyl ether; ketones such as acetone, etc.. The formulations containing these heat generating boron compounds include lotions, creams, ointments, soaps, acne sticks, powdered detergents and dry cleaning compositions. In addition, these compositions may be packaged in aerosol cans, glass and plastic containers of all kinds as well as in water miscible films.

The heat-releasing boron compound containing at least one boron-oxygen-boron bond may be either a solid or a liquid and constitutes about 20–80% and preferably 40–60% by weight of the heat generating composition.

The inert non-aqueous extending medium may be a surface active agent of the non-ionic type such as the ethylene oxide condensation products with higher fatty alcohols, higher fatty acids, higher fatty acid amides, alkylated phenols such as nonyl phenols and dinonyl phenols. Other non-ionics are the polypropylene glycols having a molecular weight greater than 900; amide and amine condensates such as fatty acid diethanolamide e.g. lauric and myristic diethanolamide, and coconut fatty acid diethanolamide. The non-ionics are the preferred class of organic surface active agents because of their miscibility with the boron compound, more specifically trimethoxyboroxine. Although, said non-ionic compounds have protic groups which should react with the instant boron compounds, experience has shown that protic groups on long chain compounds react only sluggishly, if at all, with the instant boron compounds.

However, other organic surfactants only partially miscible with the boroxide compound can also be utilized in the form of an emulsion, dispersion, or suspension.

Among the anionic compounds that may be used are the aliphatic sulfated or sulfonated detergents. Suitable examples of these aliphatic detergents are the sulfuric acid esters of polyhydric alcohols incompletely esterified with higher fatty acids, either saturated or unsaturated, particularly those whose acyl groups contain from 12 to 18 carbon atoms, e.g., coconut oil monoglyceride monosulfate, lauroyl monoglyceride monosulfate; the long chain pure or mixed higher alkyl sulfates, e.g., lauryl sulfate, cetyl sulfate, higher fatty alcohol sulfates derived from hydrogenated or non-hydrogenated coconut oil or tallow fatty acids; the higher fatty acid esters of hydroxy alkyl sulfonic acids; higher fatty acid amides of amino alkyl sulfonic acids, e.g., the oleic acid amide of amino methyl sulfonic acid, the lauric acid amide of taurine, and the like.

Other appropriate aliphatic sulf(on)ates include fatty sulfoacetates, e.g., coconut fatty alcohol sulfoacetates; sulfated fatty acyl monoethanolamides, e.g., sulfated lauroyl monoethanolamide; fatty sulfoacetamides, e.g., lauryl sulfoacetamide; lower alkyl sulfosuccinates, e.g., dioctyl sulfosuccinate; sulf(on)ated fatty oils such as sulf(on)ated castor oil and sulf(on)ated red oil, and lower alkyl esters of alphasulfonated higher fatty acids, e.g., methyl ester of alphasulfo myristic acid, sodium salt, and the alkyl sulfonates.

Synthetic detergents having a carboxylate group, and particularly the higher fatty acid amides of aliphatic amino acid compounds may also be included. A feature is the higher fatty acyl sarcosinates having about 10 to 18 carbons, usually 12-14 carbons, in the acyl radical, preferable the water-soluble salts of N-lauroyl or N-cocoyl sarcosine. Other materials are the higher fatty acid amides of polypeptide amino acids obtained by protein hydrolysis. Other suitable detergents with carboxylate groups are various cationic and amphoteric detergents described hereinafter. Suitable ether-containing sulfates may be used also such as alkylphenol polyglycol ether sulfates, e.g., lauryl phenol polyethyleneoxy sulfates, and alkyl polyglycol ether sulfates, e.g., lauryl ethyleneoxy sulfates, each containing about 10 to 18 carbons in said alkyl groups and usually averaging about 2 to 10 moles of ethylene oxide, usually 3–4 moles, per molecule.

Other anionic detergents which may be employed also include water-soluble alkyl phospates and soaps such as the sodium, potassium and triethanolamine soaps of fatty acids containing 12 to 18 carbons as well as mixtures of such soaps. Examples are sodium laurate, sodium palmitate, sodium oleate and the potassium and/or triethanolamine soaps of coconut oil, palm oil, and tallow fatty acids. Other suitable detergents are alkyl sulfonates, olefin sulfonates and alkyl phosphonates.

Cationic detergents wherein a quaternary mitrogen is part of an open chain or heterocyclic structure may also be used alone or in combination with other compatible detergents. Suitable salts are the chloride, bromide, acetate, sulfate, methosulfate and the like. Examples are lauroyl pyridinium bromide, N(lauroyl colamino formylmethyl) pyridinium chloride, cetyl trimethyl ammonium chloride, cetyl pyridinium chloride, stearyl or oleyl dimethylbenzyl ammonium chloride, distearyl dimethyl ammonium salts, stearyl amine acetate, stearyl dimethyl amine hydrochloride. Other suitable detergents are imidazolinium quaternary compounds and phosphorium salts.

Other suitable surface-active agents which can under certain conditions have a cationic nature and which may be used include the higher alkyl amine oxides such as lauryl dimethyl amine oxide. In place of the lauryl radical, other long chain alkyl radicals, preferably having 10 to 18 carbon atoms, may be used also. In place of either or both methyl radicals, there may be other lower alkyl or hydroxyalkyl radicals such as having two carbon atoms each. Suitable examples include a mixture of higher alkyl dimethyl amine oxides having essentially about 12–14 carbons in the higher alkyl groups.

Any of the usual amphoteric (ampholytic) detersive materials may be employed in the compositions of the present invention. Among those are fatty or higher alkyl imidazolines, such as 1-coco-5-hydroxyethyl-5 carboxymethyl imidazoline, and the higher alkyl beta-alanines such as dodecyl beta-alanine, said materials having usually an alkyl group of 10 to 18 carbons and the carboxylate group being in the form of the water-soluble salt. Further examples are the disodium salt of 1-lauryl-cycloimidium-2-ethoxy-ethionic acid-2-ethionic acid and its corresponding 2-lauryl sulfate derivative.

Detergents having an intermediate linkage between the hydrophobic aliphatic hydrocarbon group and the water-solubilizing sulfate, sulfonate or carboxylate group are desirable components since such materials are considered to be relatively mild and non-irritating to the skin. Such intermediate linkages are amide, ether, polyether, ester and amine groups as illustrated by the sarcosinates, imidazolines and like materials.

In addition, mixtures of organic surfactants may also be utilized in the instant invention and in some formulations are preferable. Emulsifying agents, thickening or bodying agents may be added as needed to effect the desired consistency. Therapeutic and bactericidal agents, perfumes, foaming agents, colorants, preservatives, etc. may also be added as desired.

The inert, non-aqueous carrier may also constitute waxes, lanolin, and the like. Thus, it is apparent that the inert, non-aqueous extending medium is inclusive of any substance which is compatible with but unreactive with the boron compound.

The following examples are further illustrative of the formulations of the present invention, and it is to be understood that the invention is not limited thereto.

EXAMPLE 1

Detergent Composition

|  | weight in gms. | % by weight |
|---|---|---|
| Ethoxylated nonyl phenol 73% ethoxamer | 88 | 43.6% |
| TMB (trimethoxyboroxine) | 114 | 56.4% |

The ethoxylated nonyl phenol and the TMB were mixed to give a clear solution capable of releasing heat when applied to wet hands.

EXAMPLE 2

To 47 gms. of the product of Example 1 was added 10 gms. of a condensation product of di-nonyl phenol and ethylene oxide containing 71% by weight ethoxamer to increase the detergent concentration to 53.5% by weight. This product was more viscous than that of Example 1 and exhibited better foam stability during usage.

EXAMPLE 3

To 88 gms of the product of Example 1 was added 12 gms. ethoxylated nonyl phenol containing 88% by weight ethoxamer to give a clear liquid containing 50.4% detergent. This product was comparable to that of Example 2 in performance.

EXAMPLE 4

Shaving Cream

|  | weight in gms. | % by weight |
|---|---|---|
| TMB | 67 | 54% |
| Condensation product of dinonyl phenol and 71% by weight ethoxamer | 57 | 46% |

The TMB and detergent were mixed to give a clear liquid which was placed into an aerosol container with a foam actuator and pressurized to 40 P.S.I.C. by a propellant comprising a mixture of 30% trichlorofluoromethane and 70% dichlorodifluoromethane, the propellant constituting 25%, and the shaving preparation 75% by weight of the total contents. This shaving cream gave a light foam as it was delivered from the bottle, and the heat sensation on the wet face was considerable.

EXAMPLE 5

To improve the foaming, glyceryl monostearate was added to the product of Example 4 such that the glyceryl monostearate concentration was 7.5%. This reduced the TMB to 50% and the ethoxylated nonyl phenol to 42.5%.

EXAMPLE 6

The product of Example 4 was heated under vacuum and some of the methyl borate formed was removed (removal of the methyl borate results in an increase in the boric oxide content of TMB.) The temperature was increased slowly to a maximum of 70° C. while the pressure was held at 5mm. Hg.. The resultant product was very viscous at room temperature. It was placed in an aerosol can with the same liquid propellant, as in Example 4. This shaving cream exhibited excellent foam stability as well as good body, which released heat when placed on the wet hands and face.

EXAMPLE 7

|  | % by weight |
|---|---|
| Ethoxylated nonyl phenol-63% by weight ethoxamer | 10 |
| TMB | 49 |
| Sodium tallow soap | 1 |
| Diethylene glycol dimethyl ether | 40 |

The tallow soap was mixed with TMB and the ethoxylated nonyl phenol was added thereto and stirred. The addition of diethylene glycol dimethyl ether to the above mixture yielded an oily liquid solution useful as a lotion or similar cosmetic preparation, capable of releasing heat upon contact with water or other protic material.

EXAMPLE 8

| | % by weight |
|---|---|
| Ethoxylated nonyl phenol-63% by weight ethoxamer | 30 |
| TMB | 39 |
| Sodium tallow soap | 1 |
| Diethylene glycol dimethyl ether | 30 |

The above ingredients were mixed as in Example 7 to give an oily liquid solution similar to the formulation in Example 7 which foamed and released heat when contacted with water.

EXAMPLE 9

| | % by weight |
|---|---|
| Ethoxylated nonyl phenol-63% ethoxamer | 50 |
| TMB | 50 |

The two ingredients were mixed to form a homogenous liquid having cleansing properties, and heat releasing properties in the presence of a protic solvent such as water.

EXAMPLE 10

| | % by weight |
|---|---|
| Ethoxylated nonyl phenol-63% ethoxamer | 45 |
| TMB | 45 |
| Mineral oil | 10 |

To the solution of ethoxylated nonyl phenol and TMB, mineral oil was added and stirred. The solution became opaque. It was easily washed off from the wet hands after efficiently cleansing the hands of oily and particulate dirt. It was pleasantly warm when using cold water.

EXAMPLE 11

The above formulation was placed in an aerosol container with a propellant mixture of 30% trichlorofluoromethane and 70% dichlorofluoromethane to give an aerosol shaving cream.

EXAMPLE 12

| | % by weight |
|---|---|
| Ethoxamer of mixed straight chain $C_{14}$ - $C_{18}$ alcohols with 8.5 moles of ethylene oxide per mole of alcohol | 50 |
| TMB | 50 |

The above was mixed to give a cleansing formulation which released heat upon contact with water.

EXAMPLE 13

| | % by weight |
|---|---|
| Ethoxamer of mixed straight chain $C_{14}$ - $C_{18}$ alcohols with 8.5 moles of ethylene oxide per mole of alcohol | 47.5 |
| TMB | 47.5 |
| Mineral oil | 5 |

A mixture of the three ingredients resulted in a clear solution which cleansed the skin effectively and was readily removed therefrom by washing with water. It was pleasantly warm when using cold water.

EXAMPLE 14

| | % by weight |
|---|---|
| Ethoxamer of mixed straight chain $C_{14}$ - $C_{18}$ alcohols with 8.5 moles of ethylene oxide per mole of alcohol | 45 |
| TMB | 45 |
| Mineral oil | 10 |

This yielded an opaque solution which adhered to the skin. The heat released upon contact with water was pleasantly warm.

EXAMPLE 15

| | % by weight |
|---|---|
| $B_2O_3$ | 50 |
| Ethoxylated nonyl phenol-43% by weight ethoxamer | 50 |

The resultant paste or thick lotion felt gritty and course on wet hands as well as pleasantly warm. It exhibited excellent cleansing properties, and can be particularly useful as a mechanics soap. The hands felt soft and conditioned after washing with said paste.

EXAMPLE 16

| | % by weight |
|---|---|
| $B_2O_3$ | 40 |
| Ethoxylated nonyl phenol-43% by weight ethoxamer | 40 |
| Sodium lauryl sulfate | 20 |

This paste or thick slurry exhibited all the attributes of the formulation of Example 15 and in addition possessed better foaming properties as well as being more readily removed from the hands by rinsing with water.

EXAMPLE 17

Dry Cleaning Composition

| Dry Cleaning Composition | |
|---|---|
| | % by weight |
| TMB | 50 |
| Sodium dodecyl phenol ethylene oxide (4E.O.)sulfate condensate | 50 |

The resultant solution was opaque, foamed well when contacted with water, and generated considerable heat.

EXAMPLE 18

| | % by weight |
|---|---|
| TMB | 49–50 |
| Sodium dodecyl phenol ethylene oxide (4E.O.)sulfate condensate | 49–50 |
| Mineral oil | 1–2 |

This exhibited the same characteristics as Example 17.

EXAMPLE 19

Aerosol Shave Cream

The composition of Example 18 was placed in an aerosol container and pressurized with a mixture of trichlorofluoromethane and dichlorodifluoromethane (30:70) as the propellant, yielding a pressure of 40 p.s.i.g.. A good foaming shaving cream resulted by ejection from the container.

Although trichlorofluoromethane and dichlorofluoromethane have been specifically used in the above aerosol shave cream as the propellant, any suitable non-toxic liquifiable or non-liquifiable gas or combination of gases, either organic or inorganic inclusive of nitrous oxide, carbon dioxide, nitrogen, etc.. may be substituted therefor.

Suitable propellants also include liquefied, normally gaseous, low molecular weight saturated aliphatic hydrocarbons such as propane, butane, isobutane, cyclobutane, the pentanes and hexanes; and lower halogenated hydrocarbon materials, such as halogenated methane, ethane, propane, butane, and mixtures thereof. Satisfactory products result from the use of such materials in view of their high volatility under usual atmospheric conditions, their stability in and dispersibility with the non-aqueous medium employed, etc.. Other halogenated hydrocarbon propellants which have been found to be particularly suitable for use in accordance with the present invention include monochlorodifluoromethane, monochlorodifluoromethane, dichloromonofluoroethane, dichlorotetrafluoroethane, difluoroethane, etc.. In some instances it may be desirable to use a combination of two or more of the liquefied normally gaseous materials as a propellant in order to achieve a suitable pressure within the container and impart the desired properties of stability, propellancy, ease of delivery, etc., to the shaving cream compositions.

The amount of propellant may be varied depending upon the properties desired in the final product. In general, it need only be present in an amount sufficient to satisfactorily propel or eject the shaving cream from the container in the form of a smooth lather. It has been found, however, that at least about 5% and preferably about 7 to about 10% propellant, by weight of the total shaving cream composition, should be used although higher amounts may be employed if desired, e.g., up to about 25%.

The following table defines the solubility of detergents, solvents and other additives in trimethoxyboroxine and the heat generating properties of the mixture with water.

Table II

| Additive | Solubility | Heat evolution |
| --- | --- | --- |
| Stearyl dimethyl benzyl ammonium chloride | soluble | good |
| Ethoxylated phosphate ester derived from nonyl alcohol-64% ethoxomer | soluble | good |
| Ethoxylated phosphate ester, derived from nonyl alcohol-68% ethoxomer | soluble | good |
| Disodium salt of N-tallow beta amino dipropionic acid | slightly soluble | good |
| Ethoxylated oleyl alcohol-65% ethoxomer | soluble | good |
| Polyoxyethylene (15 ETO) talloil ester | soluble | fair |
| Polyoxyethylene (5 ETO) hydrogenated tallow amide | soluble | fair |
| Triethanolamine dodecyl benzene sulfonate | soluble | good |
| Condensate of nonyl phenolpolyglycol ether with 11 moles ethylene oxide per mole nonyl phenol | soluble | good |
| Non-ionic - a liquid condensate of ethylene oxide with a hydrophobic base-20% ethoxylated, (hydrophobic base is condensate of propylene oxide and propylene glycol of M.W. 2050) | soluble | fair |
| Non-ionic - solid condensate of ethylene oxide with a hydrophobic base-80% ethoxylated, (hydrophobic base is propylene oxide condensed with propylene glycol of M.W. 3250) | soluble | good |
| Sorbitan monooleate | soluble | good |
| Lauric isopropanolamide | soluble | fair |
| Ethoxylated (3 ETO) coconut fatty acid monoethanolamide | soluble | good |
| Polyoxyethylene (40 ETO) sorbitan monopalmitate | soluble | good |

Mixtures of trimethoxyboroxine and an additive from Table 1 can be utilized per se as a self-heating cosmetic formulation. In addition, other ingredients such as thickening or bodying agents, bactericidal agents, colorants, perfumes, vitamins, hormones, etc. may be added to the above mixture without adversely affecting the heat generating properties of said cosmetics.

As shown above, trimethoxyboroxine (TMB) liberates methanol, a more or less toxic material, upon reaction with water. It will accordingly be obvious that in order to avoid even momentary contact of methanol with the skin or hair, the TMB in such cosmetic compositions as exemplified in the above formulations should be replaced by equivalent amounts of boron compounds of the above formula (A) which do not liberate methanol or other toxic by-product. More particularly, in addition to the illustrated values of $R_1$, $R_2$, $R_3$, and $R_4$ as mononuclear aryl, mononuclear aralkyl, mononuclear aroyl, cycloalkyl, acetyl, etc, the alkyl value should contain at least 2, i.e. 2–8 carbon atoms. Particularly preferred compounds for use in the above formulations and in general for treating skin and hair are the tri ($C_2$–8 alkoxy) boroxines, such as the tri-ethoxy, -propoxy, -isopropoxy and -octoxy boroxines, and bis (ethylene glycol) diborate.

It should be further understood that no claim is here made to novelty in any particular cosmetic formulation per se, i.e. the boron compounds of formula (A) above may be added in the indicated proportions to any known or desired formulation containing ingredients effective as skin cleaners, skin creams, skin lotions, shampoos, hair conditioners, hair rinses, hair bleaches, hair dyes, hair dye removers, topical pharmaceuticals, shaving preparations, and after-shave preparations and the like, provided that such formulation is devoid of any substance, such as water or other protic material described above, capable of reaction with such boron compounds. Further, for such cosmetic applications, the use of toxic materials such as methanol should of course likewise be avoided. Water is preferred for this purpose although any other non-toxic protic material may be employed with more or less equivalent exothermic results.

As indicated above admixture of the boron compound-containing cosmetic composition with even a small amount of water will pro tanto liberate heat in situ on the skin or hair being treated. Such amount of water may range from as little as about 5 up to about 100% of the stoichiometric amount of water needed to react will all the boron compound in the composition. In the recommended procedure involving pre-wetting with water of the surface to be treated, a portion of the boron compound in the applied cosmetic composition not in contact or adjacent such wetted surface may tend to remain unreacted and to that extent wasted. To promote more complete reaction of all the boron compound in the composition, it may accordingly be desirable to thoroughly mix, e.g. in atomized form, the boron compound-containing composition with the required amount of water upon or immediately prior to contact with the surface being treated and heated. This may be accomplished, for example by simultaneous application of sprays of the said composition and the water reactant or by use of a two-compartment sprayer, e.g. of the aerosol container type, enabling intimate admixture of the said composition with the water reactant in or adjacent the spray nozzle. In such case, one or more of the ingredients, preferably those readily water soluble or water dispersible, of the cosmetic composition may if desired be transferred from the non-aqueous boron compound-containing component to the water reactant component.

Formulations for shaving preparations are disclosed above containing detergents, surfactants, wetting agents, foaming agents, and/or mineral oil. Other commonly employed ingredients include soaps, germicides, fatty oils, alcohols and acids, pigments, fillers, thickeners, astringents, emollients, solubilizers, humectants, alkalizing agents, and buffers and the like. The non-aqueous shaving preparation may be foaming or non-foaming, in liquid, cream, lotion or paste form.

This invention has been disclosed with respect to preferred embodiments thereof and it will be understood that modifications and variations thereof which become obvious to those skilled in the art are to be included within the spirit and scope of the appended claims.

We claim:

1. A method of treating skin and hair with a self-heated cosmetic composition devoid of any substance capable of reaction with the boron compound defined below and selected from the group consisting of skin cleaner, skin cream, skin lotion, shampoo, shaving preparation and after-shave preparation comprising contacting the skin and hair, in the presence of water, with said composition containing about 20 to about 80% by weight of a boron compound of the formula:

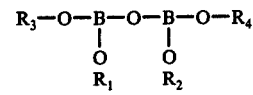

wherein $R_1$, $R_2$, $R_3$ and $R_4$ are individually $C_{2-8}$ alkyl, acetyl, mononuclear aryl, mononuclear aralkyl, mononuclear aroyl, cycloalkyl, or an ethoxylated derivative thereof, or $R_1$ and $R_3$ collectively or $R_2$ and $R_4$ collectively are:

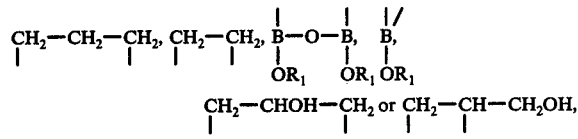

to collectively form cyclic compounds.

2. A method as defined in claim 1 wherein said boron compound is a tri ($C_{2-8}$ alkoxy) boroxine or bis (ethylene glycol) diborate.

3. A method as defined in claim 2 wherein said boron compound is triethoxy boroxine.

4. A method as defined in claim 1 wherein said composition contains an organic anionic, nonionic, cationic or amphoteric surfactant.

5. A method as defined in claim 1 wherein said composition is a shaving preparation.

6. A method as defined in claim 5 wherein said composition contains a liquified normally gaseous propellant.

7. A method as defined in claim 1 wherein such skin or hair is first wetted with water and said composition containing said boron compound is applied to the wet skin or hair.

8. A method as defined in claim 1 wherein said composition containing said boron compound is intimately mixed with the water immediately prior to contacting the skin or hair therewith.

* * * * *